US00PP13506P2

(12) United States Plant Patent
Zaiger et al.

(10) Patent No.: US PP13,506 P2
(45) Date of Patent: Jan. 21, 2003

(54) PLUM TREE NAMED 'RUBIROSA'

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 10/079,394

(22) Filed: Feb. 20, 2002

(51) Int. Cl.[7] ..... A01H 5/00

(52) U.S. Cl. ..... Plt./184

(58) Field of Search ..... Plt./184

*Primary Examiner*—Bruce R. Campell
*Assistant Examiner*—Anne Marie Grünberg

(57) ABSTRACT

A new and distinct variety of plum tree (*prunus salicina*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif. with standard commercial fruit growing practices, such as pruning, thinning, spraying, irrigation and fertilization. Its novelty consists of the following combination of desirable features:

1. Heavy and regular production of medium size, yellow flesh, clingstone fruit.
2. Fruit with an attractive red skin color.
3. Fruit with good flavor and eating quality.
4. Fruit with relative uniform size throughout the tree.

1 Drawing Sheet

BACKGROUND OF THE VARIETY

Field of the Invention

In the field of plant genetics, we conduct an extensive and continuing plant-breeding program including the organization and asexual reproduction of orchard trees, and of which almonds, apples, plums, peaches, nectarines, apricots, cherries and interspecifics are exemplary. It was against this background of our activities that the present variety of plum tree was originated and asexually reproduced by us in our experimental orchard located near Modesto, Stanislaus County, Calif.

Prior Varieties

Among the existing varieties of plum trees, which are known to us, and mentioned herein, 'Friar' Plum (non-patented), 'Autumn Giant' Plum (U.S. Plant Pat. No. 5,624), 'Red Beaut' Plum (U.S. Plant Pat. No. 2,539) and 'Burmosa' Plum (non-patented).

STATEMENT REGARDING FEDERALLY SPONSORED RESEARCH OR DEVELOPMENT

Not applicable.

ORIGIN OF THE VARIETY

The present new and distinct plum tree (*Prunus salicina*) was originated by us in our experimental orchard, located near Modesto, Calif., as a first generation cross between our proprietary parents identified as 74LA323 and 31GF169. The maternal parent (74LA323) originated from seed of a plum tree of unknown parentage. The pollen parent originated from crosses between the following, 'Friar' Plum (non-patented), 'Red Beaut' Plum (U.S. Plant Pat. No. 2,539), 'Burmosa' Plum (non-patented) and 'Autumn Giant' Plum (U.S. Plant Pat. No. 5,624). We planted and maintained a large group of these first generation seedlings, growing on their own root, under close observation, during which time the present new seedling exhibited distinct and desirable fruit characteristics and was selected in 1993 for asexual propagation and commercialization.

ASEXUAL REPRODUCTION OF THE VARIETY

Asexual reproduction of the new and distinct variety of plum tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new plum tree is of large size, vigorous, upright growth and a productive and regular bearer of medium size, firm, yellow flesh, clingstone fruit that matures in early June near Modesto, Calif. The fruit is further characterized as having a high degree of attractive red skin color, good flavor and eating quality, with a good balance between acid and sugar, and relatively uniform in size throughout the tree. In comparison to 'Red Beaut' Plum (U.S. Plant Pat. No. 2,539) the present variety has more consistent set with heavier production, and is approximately one week later in maturity. In comparison to 'Autumn Giant' Plum (U.S. Plant Pat. No. 5,624), the fruit ripens approximately 15 weeks earlier.

PHOTOGRAPH OF THE VARIETY

The accompanying color photographic illustration shows typical specimens of the foliage and fruit of the present new plum variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of plum tree, its flowers, foliage and fruit as based on observations of 7 year old specimens grown near Modesto, Calif., with color in accordance with Munsell Book of Color.

Tree:

*Size.*—Large. Pruned to 3 to 3.5 meters in height for economical harvesting of fruit.

*Vigor:*—Vigorous. Growth of 1.5 to 2 meters in height the first growing season. Varies with soil type, fertility and climatic conditions.

*Form.*—Upright, typical of normal plum growth. Usually pruned to 3 to 3.5 meters in height and vase shape.

*Branching habit.*—Upright. Crotch angle approximately 30° when juvenile, upon maturity the weight of the fruit tends to increase the branch angle.

*Productivity.*—Good production. Thinning and spacing of fruit usually necessary.

*Bearer.*—Regular. Five consecutive years of adequate fruit set, no alternate bearing observed.

*Fertility.*—Self-sterile, pollenizer required.

*Density.*—Medium dense. Pruned to remove center branches to form vase shape to allow for sunlight and air movement through center of tree to enhance fruit color and keep fruit wood healthy.

*Hardiness.*—Hardy in all stone fruit growing areas in California. Winter chilling requirement approximately 800 hours at or below 45° F. Grown in USDA Hardiness Zone 9.

Trunk:

*Size.*—Large. Average circumference of 38.1 cm at 17.8 cm above ground on a 7 year old tree.

*Stocky.*—Medium stocky.

*Texture.*—Medium shaggy, increases with age.

*Color.*—Varies from 10YR 6/2 to l0YR 7/2.

Branches:

*Size.*—Medium. Average circumference 10.2 cm at 1.2 meters above ground.

*Surface texture.*—Smooth on new growth, becomes medium rough on mature growth.

*Lenticels.*—Numerous, average of 38 in a 25.8 square cm section. Average length 3.3 mm, increases in size as branches grow larger. Average width 1.1 mm. Color 2.5YR 7/8.

*Color.*—New growth 2.5GY 6/6. Old growth 7.5YR 3/4, varies with age of growth.

Leaves:

*Size.*—Medium. Average length 82.1 mm. Average width 46.9mm.

*Form.*—Elliptical, apex acuminate, base cuneate.

*Margin.*—Serrate.

*Thickness.*—Medium, average for plums.

*Surface texture.*—Upper surface relatively smooth, slight indentation over leaf veins, glabrous. Lower surface relatively smooth, small ridges created by midrib and pinnate venation, glabrous.

*Petiole.*—Average length 13.9 mm. Average width 1.4 mm. Grooved longitudinally. Color varies from 10Y 5/6 to 10Y 6/6.

*Glands.*—Globose. Small to medium size. Average length 1 mm. Average width 0.7 mm. Number varies from 2 to 5, average number 4. Located on the upper portion of the petiole and the base of the leaf blade. Color of lower portion 5GY 6/6. Color of upper rim of gland SR 4/6.

*Color.*—Upper surface 5GY 3/4 to 5GY 4/4. Lower surface 5GY 4/4 to 5GY 5/4.

*Midvein.*—Pronounced, extends into petiole. Pinnate venation. Color 10Y 6/6.

Flower buds:

*Size*—Small. Average length 10.4 mm. Average width 4.9 mm.

*Hardiness.*—Hardy in all stone fruit growing areas of California. Grown in USDA Hardiness Zone 9.

*Form.*—Plump, free, conical, becomes elongated before opening.

*Pedicel.*—Average length 8.8 mm. Average width 0.7 mm. Color 5GY 8/8.

*Color.*—N 9/0.5.

*Number of buds per spur.*—Varies from 4 to 19, average 13.

Flowers:

*Size.*—Medium. Average height 12.5 mm. Average diameter 23.5 mm.

*Petals.*—Number —5, alternately arranged to sepals. Shape — elliptic, narrows at point of attachment. Medium. Average length 11.8 mm. Average width 6.3 mm. Color — N 9/0.5. Margin—entire, slightly cupped at apex.

*Sepals.*—Number — 5, alternately arranged to petals. Triangular shape, both upper and lower surfaces glabrous. Average length 4.1 mm. Average width 2.3 mm. Color — upper surface 5GY 6/6, lower surface 5GY 6/8.

*Stamens.*—Average number per flower —20. Average filament length 7.7 m. Filament color — N 9/0.5. Color of anthers 8.75YR 7/14.

*Pollen.*—Abundant, pollen sacs full. Self-sterile, pollenizer required. Color — 10YR 7/14.

*Pistil.*—Normally 1, varies from 1 to 2. Average length 8.9 mm, stigma averages approximately 3.5 mm below the anthers. Surfaces — glabrous. Color 2.5 Y 8/8.

*Fragrance.*—Slight to moderate aroma.

*Blooming period.*—Date of First Bloom Feb. 26, 2001. Date of Petal Fall Mar. 7, 2001. Varies slightly with climatic conditions.

*Color.*—N 9/0.5.

*Number flowers per flower bud.*—Average number 2, varies from 1 to 3.

*Pedicel.*—Average length 8.9 mm. Average width 0.8 mm. Color 5GY 8/8.

Fruit:

*Maturity when described.*—Firm ripe.

*Date of first picking.*—Jun. 3, 2001.

*Date of last picking.*—Jun. 9, 2001. Varies slightly with climatic conditions.

*Size.*—Medium. Average diameter axially 53 mm. Average transversely in suture plane 59.7 mm. Average weight 109.9 grams. Average weight varies slightly with fertility of the soil, amount of thinning and climatic conditions.

*Form.*—Globose.

*Suture.*—Nearly smooth, extends from base to apex.

*Ventral Surface.*—Nearly smooth, very slightly lipped.

*Apex.*—Rounded.
*Base.*—Varies from flat to slightly retuse.
*Cavity.*—Rounded to slightly elongated in suture plane. Average depth 4.9 mm. Average breadth 7.2 mm.

Stem:
*Size*—Medium. Average length 10.4 mm. Average diameter 1.8 mm.
*Color.*—Varies from 5Y 5/6 to 5Y 5/8.

Flesh:
*Ripens.*—Evenly.
*Texture.*—Firm, meaty.
*Fibers.*—Few, small, tender.
*Firmness.*—Good, comparable to 'Red Beaut' Plum (U.S. Plant Pat. No. 2,539).
*Aroma:*—Slight.
*Amydgalin.*—Undetected.
*Eating quality.*—Good.
*Flavor.*—Very good, good balance between acid and sugar.
*Juice*—Moderate amount, enhances flavor.
*Brix.*—Average of 14.7°, varies slightly with amount of fruit per tree and climatic conditions.
*Color.*—Varies from 5Y 8.5/8 to 5Y 8.5/10. Pit cavity color 2.5Y 6/8.

Skin:
*Thickness.*—Medium.
*Surface.*—Smooth.
*Bloom.*—Moderate amount.
*Tendency to crack.*—None.
*Color.*—Ground color varies from 7.5Y 8.5/6 to 7.5Y 8.5/8, overspread with 5R 2/6 to 5R Very small, randomly spaced areas of ground color showing at skin surface giving a speckled pattern.
*Tenacity.*—Tenacious to flesh.
*Astringency.*—None.

Stone:
*Type.*—Clingstone.
*Size.*—Medium. Average length 22.2 mm. Average width 20.1 mm. Average thickness 9.8 mm.
*Form.*—Obovate.
*Base.*—Varies from rounded to slightly retuse.
*Apex.*—Cuspidate, short in length. Average length 1.1 mm.
*Surface.*—Very lightly pitted throughout. Several small ridges extending from base towards apex. One long groove on each side of suture extending from base to apex.
*Sides.*—Varies from equal to unequal with one side extending further from the suture plane.
*Tendency to split.*—None.
*Color.*—From 2.5YR 4/8 to 2.5YR 4/10 when dry.

Kernal:
*Form.*—Obovate.
*Taste.*—Bitter, heavy amydgalin.
*Viability.*—Viable. Good embryo development.
*Size.*—Average length 14.7 mm. Average width 9.5 mm. Average depth 5.4 mm.
*Skin.*—Color 7.5YR 4/8 when dry.

Use: Dessert. Market — local and long distance.

Keeping quality: Good, held firm for 2 weeks in cold storage at 38°to 42° F. without internal break down of flesh or appreciable loss of flavor or eating quality.

Shipping quality: Good, showed minimal bruising or skin scarring in picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of plum tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of plum tree, substantially as illustrated and described, characterized by its large size, vigorous, upright growth and being a productive and regular bearer of medium size, yellow flesh, clingstone fruit with good flavor and eating quality and, in comparison to 'Red Beaut' Plum (U.S. Plant Pat. No. 2,539), the present variety has a more consistent set with heavier production and is approximately one week later in maturity.

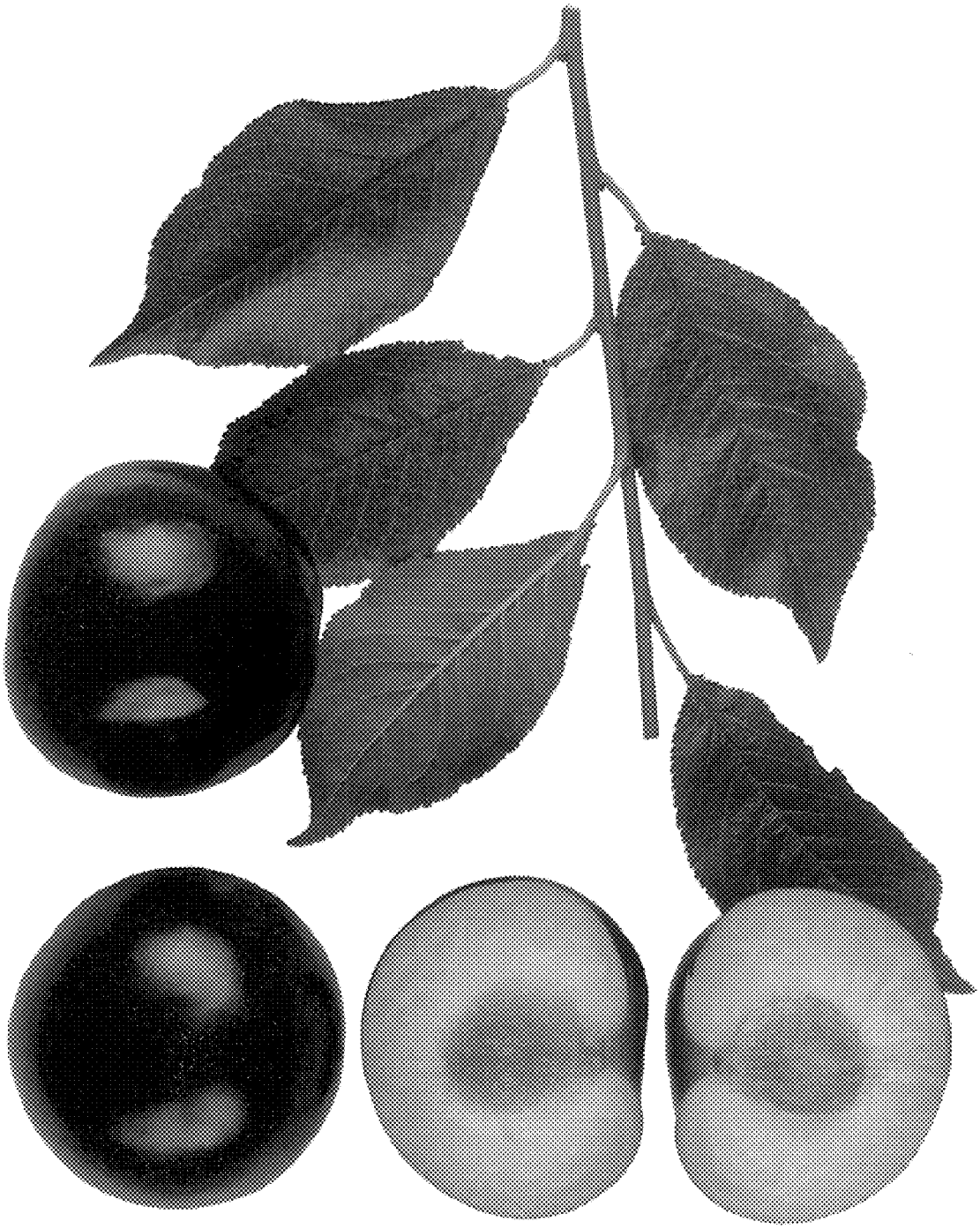

* * * * *